United States Patent
Nakamura et al.

(10) Patent No.: US 10,330,615 B2
(45) Date of Patent: Jun. 25, 2019

(54) ANALYSIS SYSTEM AND ANALYSIS METHOD

(71) Applicant: HAMAMATSU PHOTONICS K.K., Hamamatsu-shi, Shizuoka (JP)

(72) Inventors: Tomonori Nakamura, Hamamatsu (JP); Nobuyuki Hirai, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 176 days.

(21) Appl. No.: 15/516,151

(22) PCT Filed: Oct. 9, 2014

(86) PCT No.: PCT/JP2014/077099
§ 371 (c)(1),
(2) Date: Mar. 31, 2017

(87) PCT Pub. No.: WO2016/056110
PCT Pub. Date: Apr. 14, 2016

(65) Prior Publication Data
US 2017/0299534 A1 Oct. 19, 2017

(51) Int. Cl.
*G01N 25/72* (2006.01)
*G01N 17/00* (2006.01)
(Continued)

(52) U.S. Cl.
CPC ........... *G01N 25/72* (2013.01); *G01R 31/025* (2013.01); *G01R 31/2656* (2013.01); *G01R 31/311* (2013.01)

(58) Field of Classification Search
USPC ...................... 374/5, 57, 121, 161
See application file for complete search history.

(56) References Cited

U.S. PATENT DOCUMENTS 4,513,384 A * 4/1985 Rosencwaig ...... G01B 11/0633
374/134
4,965,451 A * 10/1990 Solter .................. G01N 21/171
250/330
(Continued)

FOREIGN PATENT DOCUMENTS

JP H04-249336 A 9/1992
JP 2006-319193 A 11/2006
(Continued)

OTHER PUBLICATIONS

International Preliminary Report on Patentability dated Apr. 20, 2017 for PCT/JP2014/077099.

*Primary Examiner* — Mirellys Jagan
(74) *Attorney, Agent, or Firm* — Drinker Biddle & Reath LLP

(57) ABSTRACT

A heat source position inside a measurement object is identified with high accuracy by improving time resolution. An analysis system according to the present invention is an analysis system that identifies a heat source position inside a measurement object, and includes a condition setting unit that sets a measurement point for one surface of the measurement object, a tester that applies a stimulation signal to the measurement object, a light source that irradiates the measurement point of the measurement object with light, a photo detector that detects light reflected from a predetermined measurement point on the surface of the measurement object according to the irradiation of light and outputs a detection signal, and an analysis unit that derives a distance from the measurement point to the heat source position based on the detection signal and the stimulation signal and identifies the heat source position.

12 Claims, 7 Drawing Sheets

(51) Int. Cl.
    *G01J 5/00*           (2006.01)
    *G01R 31/02*         (2006.01)
    *G01R 31/265*       (2006.01)
    *G01R 31/311*       (2006.01)

(56) References Cited

U.S. PATENT DOCUMENTS

| | | | | |
|---|---|---|---|---|
| 5,344,236 A * | 9/1994 | Fishman | ................ | G01N 25/72 |
| | | | | 356/237.5 |
| 5,352,038 A * | 10/1994 | Schmidt | ............... | G01B 11/303 |
| | | | | 250/559.39 |
| 6,074,932 A * | 6/2000 | Wu | ................... | H01L 21/76224 |
| | | | | 257/E21.546 |
| 8,152,365 B2 * | 4/2012 | Timans | ................ | G01J 5/0003 |
| | | | | 250/339.11 |
| 2013/0002283 A1 | 1/2013 | Celi et al. | | |

FOREIGN PATENT DOCUMENTS

| | | |
|---|---|---|
| JP | 2013-526723 A | 6/2013 |
| WO | WO-2011/156527 A1 | 12/2011 |
| WO | WO-2013/008850 A1 | 1/2013 |

\* cited by examiner

ANALYSIS SYSTEM AND ANALYSIS METHOD

TECHNICAL FIELD

The present invention relates to a system and a method of identifying a position of a heat source generated inside a measurement object.

BACKGROUND ART

In a related art, a system that analyzes a heat distribution of a measurement object or a position of a heat source has been known as a system that analyzes a failure portion of a measurement object (for example, see Patent Literature 1 or 2). The system of Patent Literature 1 heats wirings on a surface of a measurement object using a heating laser, acquires heat distribution information of the wirings from intensity of reflected light at the wirings, and identifies a wiring that is in a disconnected state from the heat distribution information. Further, the system of Patent Literature 2 uses a heat source generated at a failure portion (a short-circuited portion) due to application of a modulation current. The system of Patent Literature 2 applies the modulation current to a measurement object, measures heat generated by a heat source inside the measurement object using an infrared camera, and analyzes a position of the heat source (a failure portion).

CITATION LIST

Patent Literature

[Patent Literature 1] Japanese Unexamined Patent Publication No. 2006-319193
[Patent Literature 2] Japanese Unexamined Patent Publication No. 2013-526723

SUMMARY OF INVENTION

Technical Problem

Here, when a failure portion inside a measurement object is analyzed, it is necessary to identify the failure portion at each three-dimensional position with high accuracy. That is, it is necessary to identify not only a two-dimensional position on a surface of the measurement object but also a position in a depth direction from a surface of the measurement object toward an inside thereof with high accuracy. In this regard, since the system of Patent Literature 1 described above identifies a disconnected state of a wiring on a surface of a measurement object and does not analyze a failure portion in the depth direction, it is difficult for the system to be used for analysis of a failure portion inside a measurement object. Further, the system of Patent Literature 2 identifies a three-dimensional position of a heat source (a failure portion) by measuring generated heat using an infrared camera. However, since time resolution of the infrared camera is limited, the position in the depth direction of the heat source cannot be analyzed with high accuracy in some cases. For example, in a measurement object having a small thickness, a thermal response of the measurement object is fast due to a shallow heat source position. In this case, the time resolution of the infrared camera is not sufficient, and the position in the depth direction of the heat source may not be analyzed with high accuracy.

Thus, an object of the present invention is to provide an analysis system and an analysis method capable of identifying a heat source position inside a measurement object with high accuracy by improving time resolution.

Solution to Problem

An analysis system of the present invention is an analysis system that identifies a heat source position inside a measurement object, and comprises a setting unit that sets a measurement point for one surface of the measurement object; an applying unit that applies a stimulation signal to the measurement object; a light irradiation unit that irradiates the measurement point with light; a light detection unit that detects light reflected from the measurement point according to the irradiation of light and outputs a detection signal; and an analysis unit that derives a distance from the measurement point to the heat source position based on the detection signal and the stimulation signal, and identifies the heat source position.

An analysis method of the present invention is an analysis method of identifying a heat source position inside a measurement object, the analysis method including steps of: setting a measurement point for one surface of the measurement object; applying a stimulation signal to the measurement object; irradiating the measurement point with light; converting light reflected from the measurement point according to the irradiation of light into a detection signal; and deriving a distance from the measurement point to the heat source position based on the detection signal and the stimulation signal and identifying the heat source position.

In the analysis system and the analysis method, a stimulation current is applied to the measurement object that is irradiated with the light. If there is a short-circuited portion inside the measurement object, the short-circuited portion generates heat and becomes a heat source according to the application of the stimulation current. In a state in which the heat source is generated, light reflected from the measurement point set for the one surface of the measurement object according to irradiated light is detected, and a detection signal is output. In the state in which the heat source is generated, a reflectance of the light changes according to the heat from the heat source. Since a thermal response from the heat source quickens in inverse proportion to a distance from the heat source to the measurement point, it is possible to estimate the distance from the measurement point to the heat source position by analyzing the detection signal of the light of which the reflectance changes according to the heat from the heat source. Thus, by identifying the heat source position using a scheme of analyzing the detection signal according to the reflected light, it is possible to improve time resolution in comparison with a method in which an integration (shutter) time of about 1 ms to 10 ms is required, for example, as in an infrared camera. Further, if the one surface of the measurement object is, for example, a surface on which materials with different refractive indexes are in contact with each other, a change in reflectance is maximized on the one surface, and accordingly, it is possible to detect light in which the change in reflectance according to the heat of the heat source is appropriately reflected by detecting the light reflected from the surface. Thus, according to the present invention, it is possible to identify the heat source position inside the measurement object with high accuracy.

Further, in the analysis system and the analysis method of the present invention, the analysis unit may derive a phase delay amount of the detection signal relative to the stimulation signal to derive the distance from the measurement point to the heat source position and identify the heat source position. The phase delay amount of the detection signal relative to the stimulation signal changes according to a temporal change in the reflectance of the reflected light. Therefore, it is possible to derive the distance to the heat source position by deriving the phase delay amount of the detection signal and identify the heat source position. The derivation of the phase delay amount can be easily performed. Further, since the phase delay amount and a temporal change in the reflectance have a close correspondence relationship, it is possible to identify the heat source position easily and with high accuracy by deriving the phase delay amount of the detection signal.

Further, in the analysis system and the analysis method of the present invention, the analysis unit may identify the heat source position by two-dimensionally mapping the phase delay amount. By performing the two-dimensional mapping on the phase delay amount, it is possible to analyze the heat source position more easily and with high accuracy. Further, for example, even when the heat source is at two or more points, it is possible to analyze the heat source position easily and with high accuracy.

Further, in the analysis system and the analysis method of the present invention, the setting unit may set at least three measurement points for the measurement object, and the analysis unit may derive a distance from each of the at least three set measurement points to the heat source position and identify the heat source position. It is necessary to identify the heat source position as a three-dimensional position. It is possible to identify the heat source position by deriving the phase delay amount at the at least three points.

Further, in the analysis system and the analysis method of the present invention, the setting unit may set at least four measurement points for the measurement object, and the analysis unit may derive a distance from each of the at least four set measurement points to the heat source position. In this case, it is possible to estimate a heat source position candidate region on the one surface of the measurement object based on the derived distance.

Further, the analysis system of the present invention may further include an infrared camera unit that acquires an infrared image of the measurement object. Since a rough heat source position can be identified using the infrared image acquired by the infrared camera unit, it is possible to simplify identification of the heat source position using the analysis unit.

Further, in the analysis system and the analysis method of the present invention, the setting unit may set the measurement point based on the infrared image acquired by the infrared camera unit. Since a rough heat source position on the one surface of the measurement object can be identified using the infrared image, it is possible to set the measurement point at a more appropriate position.

Further, in the analysis system of the present invention, the analysis unit may derive the distance from the measurement point to the heat source position based on the derived phase delay amount and a heat propagation velocity determined according to the measurement object and analyze the heat source position. Since the distance to the heat source position is derived from the phase delay amount and the heat propagation velocity easily and with high accuracy, it is possible to identify the heat source position easily and with high accuracy.

Further, in the analysis system of the present invention, the analysis unit may store a table defining a correspondence relationship between the phase delay amount of the detection signal and the distance from the measurement point to the heat source position in advance, and derive the distance from the measurement point to the heat source position based on the derived phase delay amount and the table to analyze the heat source position. By deriving the distance to the heat source position using the table defining the correspondence relationship between the phase delay amount and the distance to the heat source, which has been stored in advance, it is possible to identify the heat source position easily and with high accuracy.

Further, in the analysis system of the present invention, the light irradiation unit may include a light source that outputs light and an optical scanner that irradiates a measurement point with light. Thus, it is possible to appropriately irradiate the set measurement point with light.

Advantageous Effects of Invention

According to the present invention, it is possible to identify a heat source position inside a measurement object with high accuracy by improving time resolution.

DESCRIPTION OF EMBODIMENTS

Figure 1:
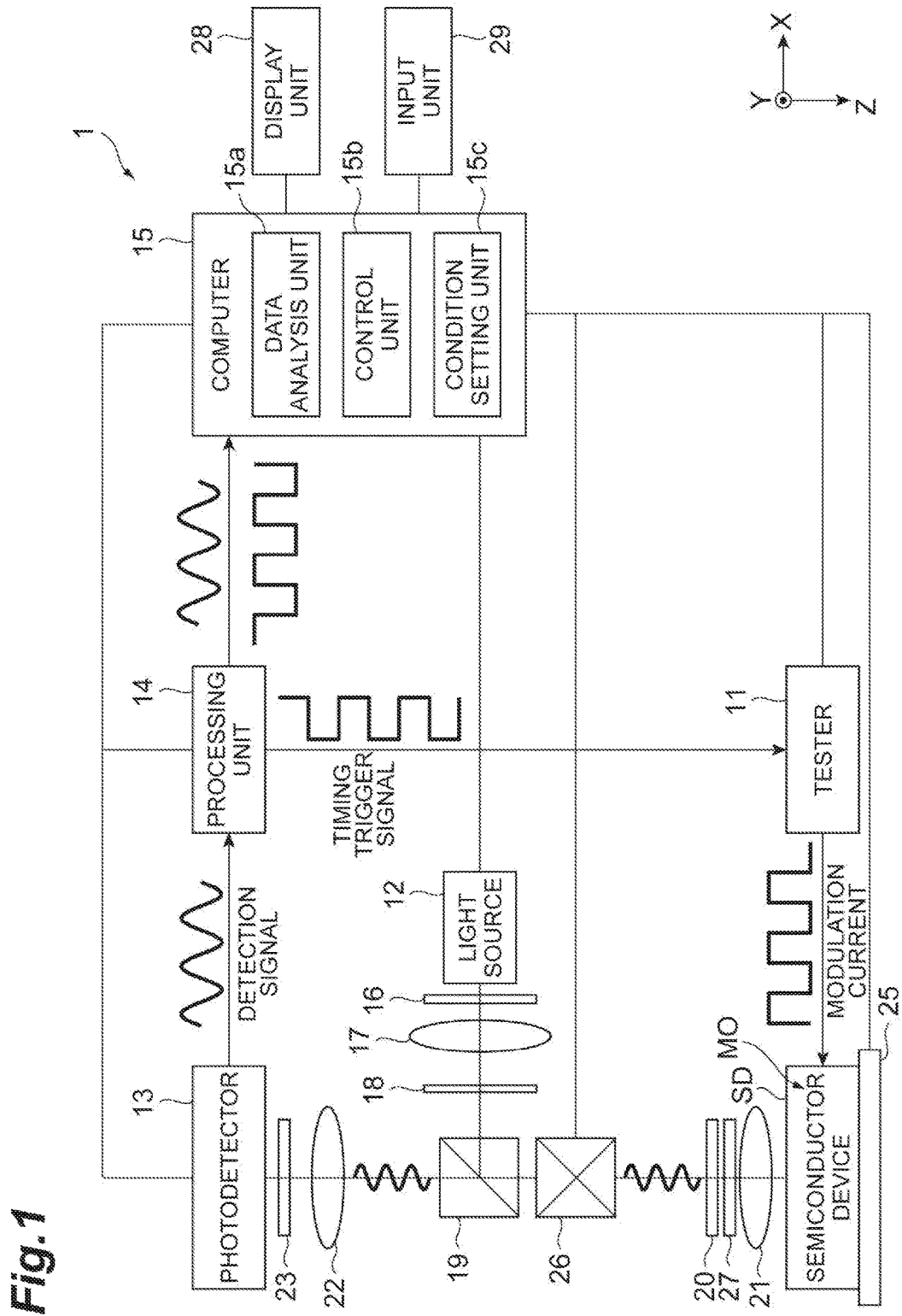
FIG. 1 is a configuration diagram of an analysis system according to a first embodiment of the present invention.

Hereinafter, preferred embodiments of the present invention will be described in detail with reference to the drawings. In respective figures, the same or corresponding portions are denoted with the same reference numerals, and repeated description will be omitted.

First Embodiment

As illustrated in FIG. 1, an analysis system 1 according to a first embodiment is an analysis system that identifies a heat source position in a measurement object (which will be described below in detail) such as a semiconductor device SD, which is a device under test (DUT). A heat source is a heat generating portion inside the measurement object. If there is a short-circuited portion or the like inside the measurement object when a signal is applied to the measurement object, the short-circuited portion generates heat and becomes a heat source. That is, the analysis system 1 is a failure analysis system that analyzes an abnormality of a short-circuited portion or the like inside a measurement object by identifying a heat source position.

For example, an integrated circuit having a PN junction of a transistor or the like (for example, a small scale integration (SSI), a medium scale integration (MSI), a large scale integration (LSI), a very large scale integration (VLSI), an ultra large scale integration (VLSI), or a giga scale integration (GSI)), a MOS transistor and a bipolar transistor for large current/high voltage, or a memory storage device can be used as the device under test. In the following description, it will be assumed that the device under test is an integrated circuit.

Figure 2:
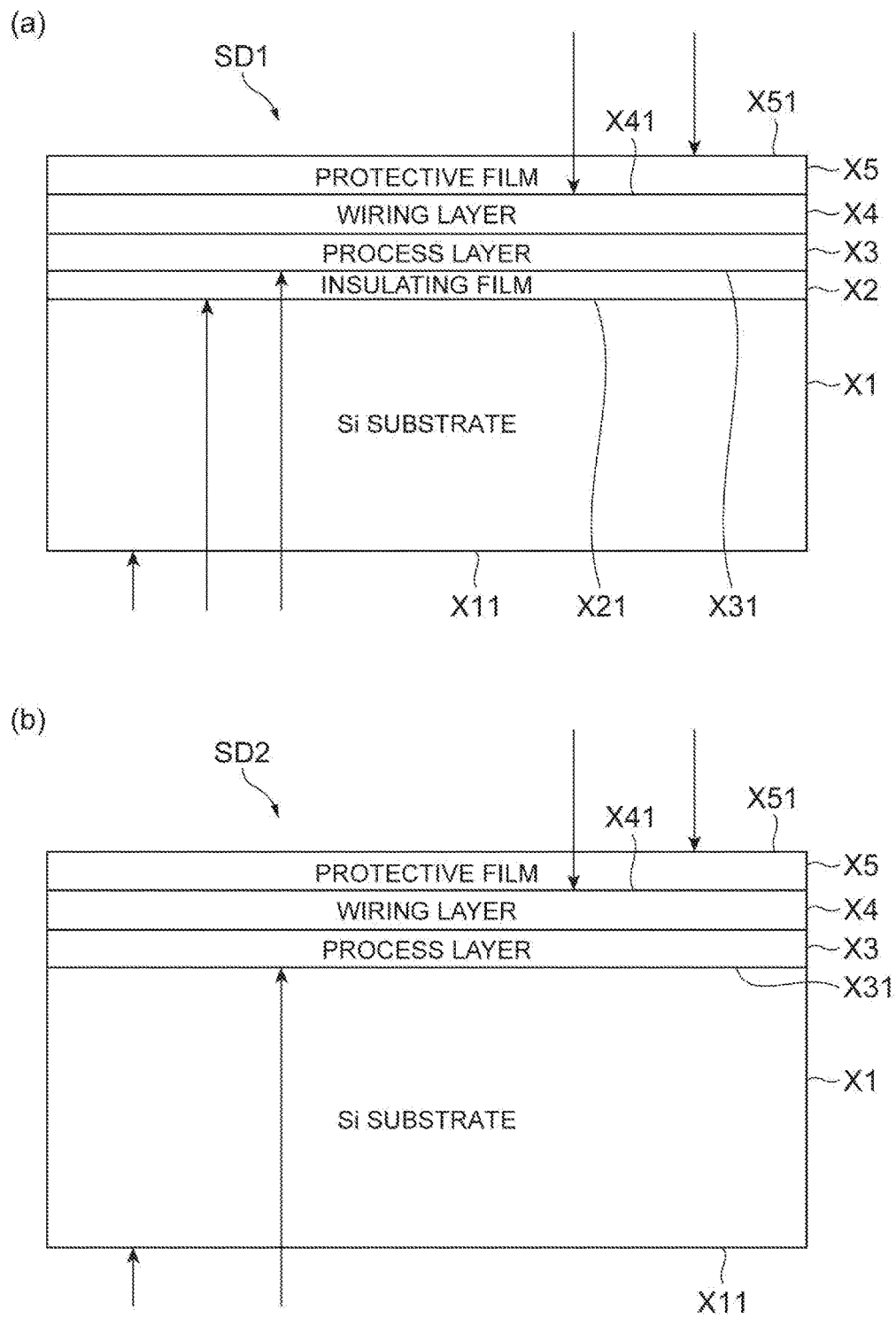
FIG. 2 is a diagram illustrating a semiconductor device.

The semiconductor device SD will be described with reference to FIG. 2. FIG. 2(a) illustrates a semiconductor device SD1 as an example of the semiconductor device SD, and FIG. 2(b) illustrates a semiconductor device SD2 as an example of the semiconductor device SD. As illustrated in FIG. 2(a), in the semiconductor device SD1, an insulating film X2 is stacked on a Si substrate X1. Further, a process layer X3 is stacked on the insulating film (a SiO2 layer) X2, a wiring layer X4 is stacked on the process layer X3, and a protective film X5 is stacked on the wiring layer X4. Here, a portion that can be a heat generating portion due to a short circuit is a device layer including the process layer X3 and the wiring layer X4. If the device layer is a measurement object, a surface of the measurement object is, for example, a surface X41 that is in contact with the protective film X5 in the wiring layer X4 and a surface X31 that is in contact with the insulating film X2 in the process layer X3. Further, if the measurement object is also the protective film X5 and the insulating film X2, in addition to the device layer, a surface of the measurement object is, for example, a surface X51 of the protective film X5 that is in contact with air and a surface X21 of the insulating film X2 that is in contact with the Si substrate X1. Further, if the measurement object is also the Si substrate X1, a surface of the measurement object is, for example, the surface X51 of the protective film X5 that is in contact with air and a surface X11 of the Si substrate X1 that is in contact with air.

The semiconductor device SD2 illustrated in FIG. 2(b) has substantially the same configuration as the semiconductor device SD1 illustrated in FIG. 2(a), and is different from the semiconductor device SD1 in that there is no insulating film X2 and the process layer X3 is stacked on a Si substrate X1. In the semiconductor device SD2, when a device layer including the process layer X3 and a wiring layer X4 is a measurement object, a surface of the measurement object is, for example, a surface X41 in contact with a protective film X5 in the wiring layer X4 and a surface X31 that is in contact with the Si substrate X1 in the process layer X3. Further, if the measurement object is the protective film X5, in addition to the device layer, a surface of the measurement object is, for example, a surface X51 of the protective film X5 that is in contact with air and the surface X31 in contact with the Si substrate X1 in the process layer X3. Further, if the measurement object is also the Si substrate X1, a surface of the measurement object is, for example, the surface X51 of the protective film X5 that is in contact with air and a surface X11 of the Si substrate X1 that is in contact with air. In the following description, it will be assumed that the semiconductor device SD is the semiconductor device SD1, and the process layer X3, the wiring layer X4, the protective film X5, and the insulating film X2 are measurement objects MO in this embodiment. Further, a surface of the measurement object MO described above may be described as a surface of the measurement object.

Referring back to FIG. 1, the analysis system 1 includes a tester 11 (an applying unit), a light source 12 (a light irradiation unit), a photodetector 13 (a light detection unit), a processing unit 14, a computer 15, a display unit 28, and an input unit 29. The computer 15 includes a data analysis unit 15a (an analysis unit), a control unit 15b, and a condition setting unit 15c (a setting unit). The semiconductor device SD is placed on a stage 25.

The tester 11 outputs a modulation current (a stimulation signal) and applies the modulation current to the measurement object MO of the semiconductor device SD. The semiconductor device SD is driven by the modulation current applied by the tester 11. Further, when a short-circuited portion is included inside the measurement object MO, the short-circuited portion generates heat and becomes a heat source due to the applied modulation current. That is, the tester 11 generates a heat source inside the semiconductor device SD by applying the modulation current to the measurement object MO. Based on a timing trigger signal input from the processing unit 14, the tester 11 generates and outputs a modulation current having the same frequency as the timing trigger signal and a phase synchronized to that of the timing trigger signal.

The light source 12 irradiates the measurement object MO with light (irradiated light). The light source 12 includes a super luminescent diode (SLD). The light source 12 may be, for example, a laser light source such as a laser diode (LD) or a light source using a light emitting diode (LED) or a lamp light source. Further, the irradiated light may be CW light or may be pulsed light. A wavelength of the irradiated light is, for example, about 1.3 μm, and a refractive index in the measurement object MO mainly formed of silicon is about 3.5.

The irradiated light output from the light source 12 is input to a polarizer 18 via a pinhole 16 and a lens 17. The polarizer 18 transmits only irradiated light polarized in a specific direction, and the irradiated light transmitted through the polarizer 18 is input to a polarization beam splitter (hereinafter referred to as a PBS) 19. The PBS 19 transmits the light polarized in a specific direction and reflects the light polarized in a specific direction. The PBS 19 reflects the irradiated light transmitted through the polarizer 18 toward an optical scanner 26 (a light irradiation unit). The optical scanner 26 is, for example, a galvano mirror scanner, a polygon mirror scanner, an MEMS mirror scanner, or the like, and is controlled so that a desired position of the measurement object MO is irradiated with the light from the PBS 19. The polarizer 18 may be omitted if the polarizer 18 is not necessary.

The irradiated light output from the optical scanner 26 passes through a short pass filter 27 and is radiated toward the measurement object MO of the semiconductor device SD via a λ/4 plate 20 and a lens 21. More specifically, the irradiated light is radiated toward a measurement point set on the surface of the measurement object MO that will be described below.

Light (reflected light) reflected from the measurement point in response to the irradiated light passes through the lens 21, the short pass filter 27, the λ/4 plate 20, and the optical scanner 26 again and is input to the PBS 19. In this case, the short pass filter 27 can shield infrared rays generated in the measurement object MO. Further, since a polarization direction of the light input to the PBS 19 is tilted due to the light input to the PBS 19 being transmitted through the λ/4 plate 20 twice, the PBS 19 transmits the reflected light. The reflected light is input to the photodetector 13 via a lens 22 and a pinhole 23. Thus, in the optical system of this embodiment, a confocal optical system is used and is configured so that reflected light from a limited focus range can be detected. Although the pinholes 16 and 23 are used in this embodiment, the confocal optical system may be realized using a difference in refractive index between a core and a cladding using an optical fiber.

The photodetector 13 detects the reflected light reflected from the surface of the measurement object MO according to the irradiated light. Further, the photodetector 13 converts the detected reflected light into a detection signal, which is an analog signal, and outputs the detection signal. The photodetector 13 is an avalanche photodiode (APD), a photodiode (PD), a photo multiplier tube (PMT), or the like. Here, in a state in which a heat source is generated, a material refractive index of the measurement object MO changes according to heat from the heat source, and a reflectance of the reflected light changes. Such a temporal change in the reflectance of the reflected light appears as a temporal change of the detection signal output from the photodetector 13. That is, the temporal change in the detection signal output from the photodetector 13 changes according to a speed of the thermal response that the measurement point receives from the heat source. Naturally, the speed of the thermal response that the measurement point receives from the heat source is higher as the measurement point nears the heat source. The detection signal output from the photodetector 13 is input to the processing unit 14.

The processing unit 14 outputs the timing trigger signal to the tester 11 and the computer 15. Based on the timing trigger signal, the tester 11 generates a modulation current having the same frequency as that of the timing trigger signal and a phase synchronized to that of the timing trigger signal. Further, if the detection signal is input, the processing unit 14 outputs the detection signal to the computer 15.

The computer 15 includes a data analysis unit 15a that identifies a heat source position of the measurement object MO based on the detection signal and the stimulation signal, a condition setting unit 15c that sets the measurement point on the surface of the measurement object MO, and a control unit 15b that controls the photodetector 13, the processing unit 14, the optical scanner 26, the tester 11, and the stage 25. The computer 15 is also connected to the display unit 28 that displays an analysis result or an image such as a pattern image of the semiconductor device SD or the input unit 29 that inputs an analysis condition.

The condition setting unit 15c sets the measurement point on the surface of the measurement object MO. Specifically, a user indicates at least one measurement point using the input unit 29 while viewing the display unit 28 on which the pattern image of the semiconductor device SD is displayed. The pattern image is, for example, an LSM image or the like. The condition setting unit 15c sets position information (an x coordinate and a y coordinate) on the surface of the measurement object MO based on the position information of the indicated measurement point.

The control unit 15b controls the optical scanner 26 based on the position information of the measurement point set by the condition setting unit 15c. Specifically, the control unit 15b controls the optical scanner 26 based on the position information of the measurement point so that the measurement point on the surface of the measurement object MO is irradiated with light.

Figure 3:
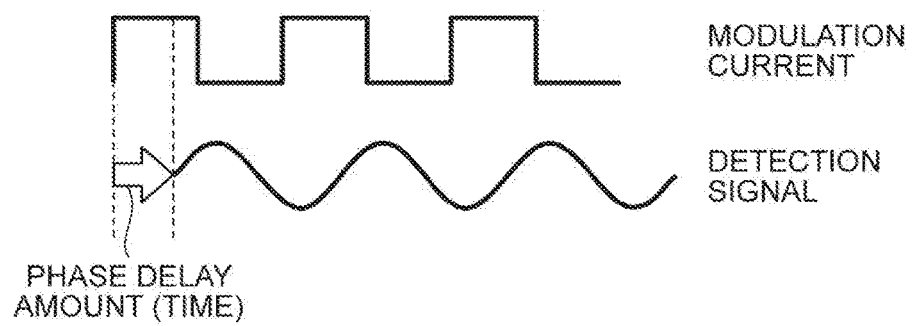
FIG. 3 is a diagram illustrating a phase delay amount of a detection signal.

The data analysis unit 15a identifies the heat source position of the measurement object MO based on the detection signal. Specifically, the data analysis unit 15a derives a phase delay amount (see FIG. 3) of the detection signal relative to the modulation current to derive a distance from a point (the measurement point) at which the light is reflected on the surface of the measurement object MO to the heat source position and identify the heat source position. Since the modulation current is a signal having the same frequency as that of the timing trigger signal and a phase synchronized to that of the timing trigger signal, the data analysis unit 15a can derive the phase delay amount (see FIG. 3) of the detection signal relative to the modulation current based on the timing trigger signal and the detection signal input from the processing unit 14. As described above, since the phase of the detection signal changes according to the distance from the measurement point to the heat source, the phase delay amount of the detection signal relative to the modulation current also changes according to the distance from the measurement point to the heat source. Specifically, the phase delay amount of the detection signal increases in proportion to the distance from the measurement point to the heat source.

The data analysis unit 15a obtains the distance from the measurement point on the surface of the measurement object MO to the heat source from the derived phase delay amount. More specifically, the data analysis unit 15a derives the distance from the measurement point to the heat source by multiplying the derived phase delay amount by a heat propagation velocity determined according to the measurement object MO. If v (m/s): heat propagation velocity, f (kHz): frequency of the modulation current, K (W/m/k): thermal conductivity of the measurement object MO, q (J/g/k): specific heat of the measurement object MO, and ρ (kg/m$^{-3}$): density of the measurement object MO, a heat propagation velocity v can be obtained using Equation (1) below.

[Math. 1]

$$v = 2\pi\sqrt{f}\sqrt{\frac{K}{\rho q \pi}} \quad (1)$$

The data analysis unit 15a may store a table defining a correspondence relationship between the phase delay amount and the distance from the measurement point to the heat source in advance, and derive the distance from the measurement point to the heat source based on the derived phase delay amount and the table.

The data analysis unit 15a analyzes the heat source position based on the derived distance from the measurement point to the heat source. Specifically, the data analysis unit 15a derives the phase delay amount of the detection signal at each of three measurement points on the surface of the measurement object MO, and derives a distance from each of the measurements point to the heat source. A three-dimensional heat source position is uniquely identified based on the distance to the heat source at each of the three measurement points. Hereinafter, identification of the heat source position by the data analysis unit 15a will be described with reference to FIG. 4.

Figure 4:
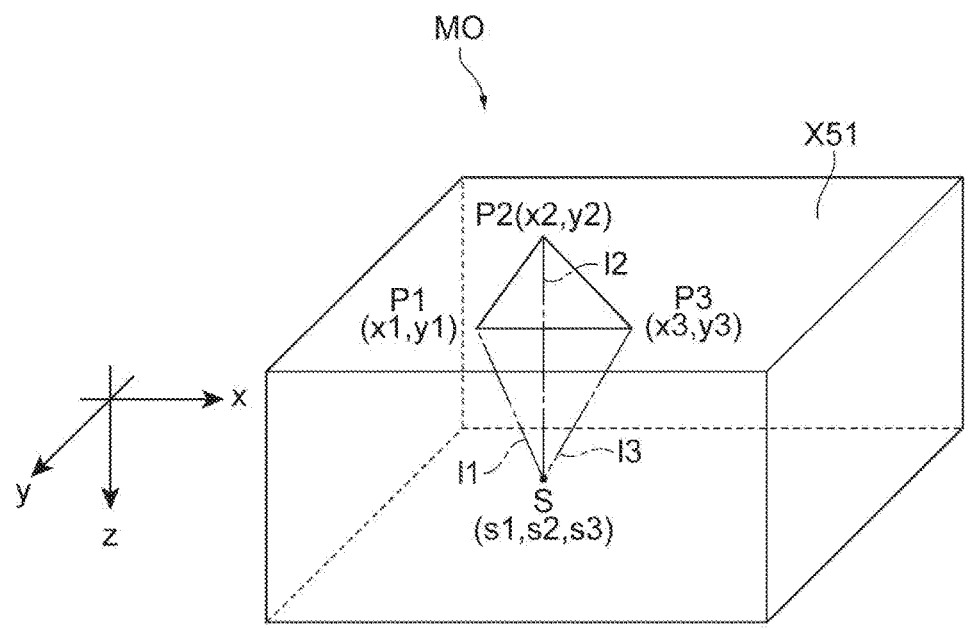
FIG. 4 is a diagram illustrating an analysis image of a heat source position by three-point measurement.

FIG. 4 is a diagram schematically illustrating only a portion of the measurement object MO in the semiconductor device SD. A Z-axis direction in FIG. 4 is an optical axis direction of the irradiated light and is a stacking direction of the measurement object MO (the semiconductor device SD). Further, an X-axis direction in FIG. 4 is a direction perpendicular to the Z-axis direction, and a Y-axis direction is a direction perpendicular to the Z-axis direction and the X-axis direction. Therefore, a plane perpendicular to the Z-axis direction is formed by the X-axis and the Y-axis.

In the data analysis unit 15a, each of the parameters (v (m/s): heat propagation velocity, f (kHz): frequency of the modulation current, K (W/m/k): thermal conductivity of the measurement object MO, q (J/g/k): specific heat of the measurement object MO, and ρ (kg/m$^{-3}$): density of the measurement object MO) of Equation (1) described above are set in advance, and the heat propagation velocity is calculated and stored. First, the data analysis unit 15a stores coordinates (x1, y1) of a measurement point P1 set by the condition setting unit 15c. The data analysis unit 15a derives a phase delay amount of a detection signal based on a detection signal converted from reflected light at the measurement point P1 and the modulation current (the timing trigger signal). Further, the data analysis unit 15a derives a distance l1 from the measurement point P1 to a heat source S based on the phase delay amount and the stored heat propagation velocity.

Similar to the derivation process at the measurement point P1, the data analysis unit 15a stores coordinates (x2, y2) and (x3, y3) for different measurement points P2 and P3, calculates a phase delay amount based on detection signals converted from reflected light at the measurement points P2 and P3 and the modulation current, and derives a distance l2 from the measurement point P2 to the heat source S and a distance l3 from the measurement point P3 to the heat source S based on the phase delay amount and the heat propagation velocity. Finally, the data analysis unit 15a calculates a three-dimensional position (s1, s2, s3) of the heat source S from the coordinates (x1, y1), (x2, y2) (x3, y3) of the respective measurement points P1, P2, and P3 and the distances l1, l2, and l3 from the respective measurement points P1, P2, and P3 to the heat source S. Through the above process, the data analysis unit 15a identifies the heat source position. According to this scheme, even when there is no position information of the heat source position, the data analysis unit 15a can identify the heat source position by setting at least three measurement points.

If four or more measurement points are set, measurement may be performed while narrowing down a region where a heat source position exists. For example, the region where the heat source position exists can be estimated by randomly setting the four or more measurement points on the surface of the measurement object MO, deriving a distance between each of the measurement points and the heat source position, and comparing the distances. The data analysis unit 15a can identify the heat source position by resetting a measurement point in an estimation region, narrowing down the region where the heat source region exists, and finally, setting at least three measurement points.

Further, if the data analysis unit 15a identifies the heat source position from phase delay amounts, for example, at three measurement points, the data analysis unit 15a may analyze the heat source position by two-dimensionally mapping the phase delay amounts of the respective measurement points. More specifically, the data analysis unit 15a may map the phase delay amount to the coordinates of each of the measurement points using the above-described X-axis and Y-axis as two axes of the coordinates. In this case, it is easy to visually recognize the heat source position from a two-dimensional map, for example, even when there are two or more heat sources.

Next, an operation and an effect of the analysis system 1 according to this embodiment will be described.

In a related art, a method of identifying a heat source position by applying a modulation current to a measurement object and measuring heat generated by a heat source inside the measurement object using an infrared camera is known. In this measuring method, a two-dimensional position with no consideration of a depth direction of the heat source can be simply identified from a detection signal (captured image) from the infrared camera. On the other hand, it is necessary for the position in the depth direction of the heat source to be identified from a delay amount (phase delay amount) of the detection signal relative to the modulation current. The infrared camera sets black body radiation energy in which a color of radiated light changes according to a temperature as a measurement object. Whether or not the infrared camera can acquire an image with sensitivity (an S/N ratio) in which the delay amount of the detection signal can be derived depends on the amount of heat (a heat radiation amount) radiated from the measurement object. Generally, an integration (shutter) time of about 1 ms to 10 ms is required in order to acquire an image (with sufficient sensitivity) from which the delay amount of the detection signal can be derived.

Therefore, time resolution the delay amount of the detection signal is derived using the method in the related art is limited (for example, about 100 Hz). Here, if a thickness of the measurement object is small (for example, 20 μm or less if the measurement object is a circuit structure formed on a single layer LSI), a heat propagation distance is short due to a shallow heat source position, and a thermal response of the measurement object is fast. In this case, in the time resolution described above, the thermal response of the measurement object cannot be sufficiently measured, and accuracy of an analysis of the heat source position may be degraded. Specifically, an analysis error of the heat source position may be about 5 μm due to the limited time resolution described above.

In the analysis system 1 according to this embodiment, the modulation current is applied to the measurement object MO that is irradiated with light. If there is a short-circuited portion inside the measurement object MO, the short-circuited portion generates heat and becomes a heat source according to the application of the modulation current. In a state in which the heat source is generated, reflected light reflected from the measurement point according to the irradiated light is detected, and a detection signal is output. In the state in which the heat source is generated, reflectance of the reflected light changes over time according to the heat from the heat source. Since a thermal response from the heat source detected at the measurement point quickens in inverse proportion to a distance from the heat source to the measurement point, it is possible to estimate the distance from the measurement point to the heat source by analyzing the detection signal of the reflected light of which the reflectance changes over time according to the heat from the heat source. Thus, by identifying the heat source position using optical probing in which the detection signal according to the reflected light of the measurement object MO is analyzed, it is possible to improve the time resolution in comparison with a method in which an integration (shutter) time of about 1 ms to 10 ms is required as in an infrared camera. By improving the time resolution, it is possible to appropriately measure a thermal response and to improve analysis accuracy of the heat source position even when a thickness of the measurement object is small and a thermal response is fast. Specifically, if probe light intensity equal to or greater than certain intensity can be ensured, the time resolution has sub-nanosecond accuracy and an analysis error of the heat source position can be 100 nm or less.

Further, since the change in reflectance of the reflected light is maximized on the surface of the measurement object MO, which is a surface on which materials with different refractive indexes are in contact with each other, it is possible to detect reflected light in which a change in reflectance according to the heat of the heat source is appropriately reflected by detecting the reflected light reflected from the surface of the measurement object MO. That is, it is possible to analyze the heat source position with high accuracy.

Further, in a measurement method using only an infrared camera of the related art, since the infrared camera detects black body radiation, the infrared camera cannot help simultaneously detecting infrared rays that are generated from objects other than the heat source. Under influence of such noise, analysis accuracy of a heat source position may be degraded. On the other hand, since the analysis system 1 detects heat from the reflected light on the surface of the measurement object MO, it is possible to reduce the influence of noise and perform a measurement influenced only by the heat source. Thus, it is possible to improve analysis accuracy of a heat source position.

Further, in the analysis system 1, the data analysis unit 15*a* derives the phase delay amount of the detection signal relative to the timing trigger signal (that is, the modulation current) to derive the distance from the measurement point of the measurement object MO to the heat source position and analyze the heat source position. The phase delay amount of the detection signal relative to the modulation current changes according to a temporal change in the reflectance of the reflected light. Therefore, it is possible to analyze the heat source position by deriving the phase delay amount of the detection signal. The derivation of the phase delay amount can be easily performed. Further, since the phase delay amount and the temporal change in the reflectance have a close correspondence relationship, it is possible to analyze the heat source position easily and with high accuracy by deriving the phase delay amount of the detection signal.

Further, in the analysis system 1, the data analysis unit 15*a* may analyze the heat source position by performing two-dimensional mapping on the phase delay amount of the measurement point. By performing the two-dimensional mapping on the phase delay amount of the measurement point, it is possible to visually confirm the phase delay amount at each measurement point and to analyze the heat source position more easily and with high accuracy. Further, for example, even when the heat source is at two or more points, it is possible to analyze the heat source position easily and with high accuracy.

Further, in the analysis system 1, the data analysis unit 15*a* may derive the phase delay amount of the detection signal at at least three measurement points of the surface of the measurement object MO. It is necessary to identify the heat source position as a three-dimensional position. By deriving the phase delay amount at at least three points, it is possible to identify the heat source position while reducing the number of measurements as much as possible.

Further, in the analysis system 1, the data analysis unit 15*a* may derive the phase delay amount of the detection signal at at least four or more measurement points of the surface of the measurement object MO. It is possible to analyze the heat source position with higher accuracy since the heat source position can be narrowed down and detected.

Further, in the analysis system 1, the data analysis unit 15*a* may derive the distance from the measurement point to the heat source on the surface of the measurement object MO based on the derived phase delay amount and the heat propagation velocity determined according to the measurement object MO and analyzes the heat source position. Since the distance from the measurement point to the heat source is derived easily and with high accuracy from the phase delay amount and the heat propagation velocity, it is possible to analyze the heat source position easily and with high accuracy.

Further, in the analysis system 1, the data analysis unit 15*a* may store a table defining a correspondence relationship between the phase delay amount of the detection signal and the distance from the measurement point to the heat source on the surface of the measurement object MO in advance, derive the distance from the measurement point to the heat source on the surface of the measurement object MO based on the derived phase delay amount and the table, and analyze the heat source position. By deriving the distance from the measurement point to the heat source using the table defining the correspondence relationship between the phase delay amount and the distance to the heat source, which has been stored in advance, it is possible to analyze the heat source position easily and with high accuracy.

Second Embodiment

Next, an analysis system 1A according to a second embodiment will be described with reference to FIGS. 5 and 6. In the description of this embodiment, a difference between this embodiment and the first embodiment described above will be mainly described.

Figure 5:
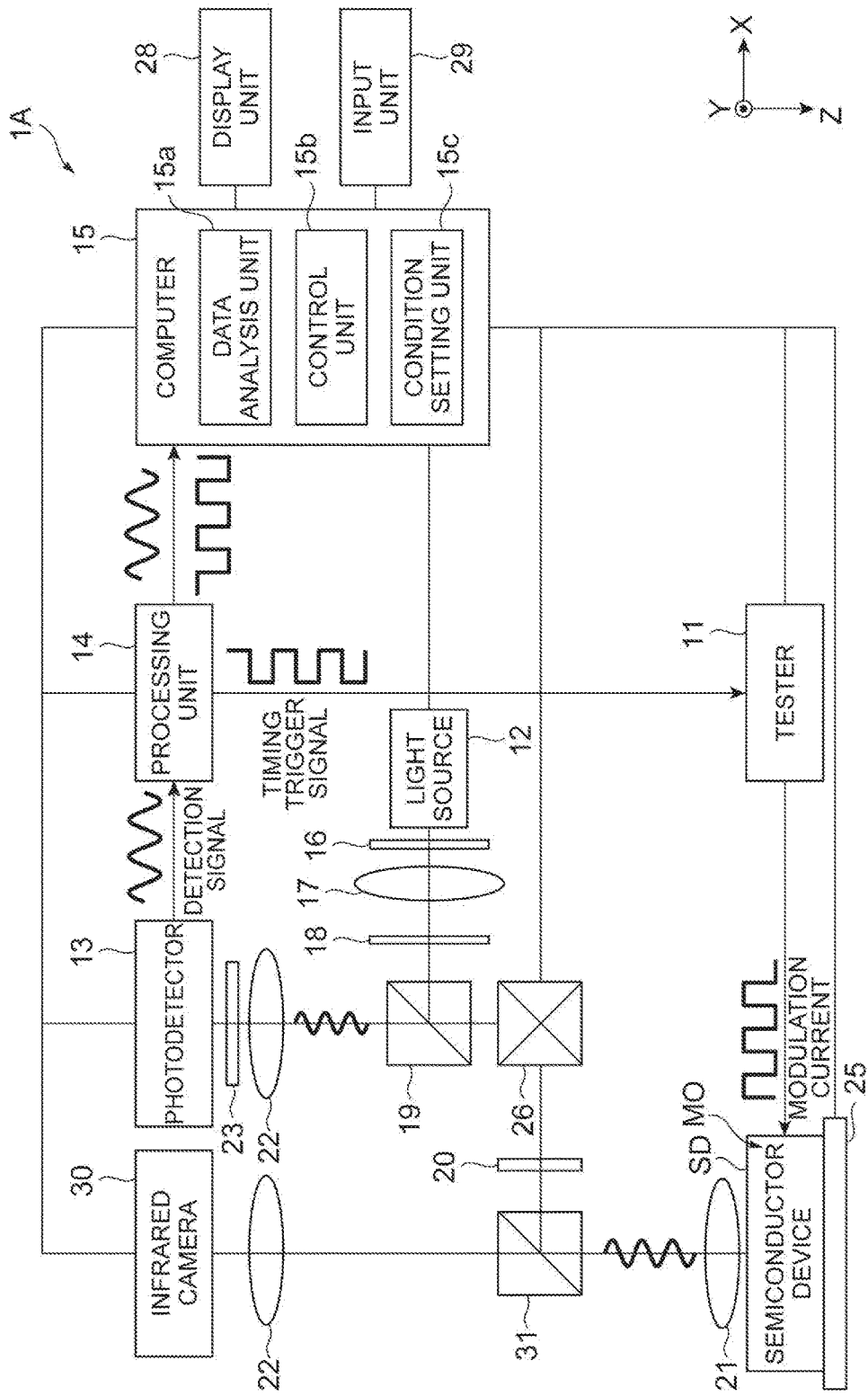
FIG. 5 is a configuration diagram of an analysis system according to a second embodiment of the present invention.

As illustrated in FIG. 5, the analysis system 1A according to the second embodiment has the same configuration as the configuration of the analysis system 1 with respect to a configuration for performing optical probing. Further, the analysis system 1A includes an infrared camera 30 (an infrared camera unit) that detects infrared rays from a measurement object MO including infrared rays from a heat source of the measurement object MO, and a dichroic mirror 31 that divides light from a lens 21 into light in an infrared wavelength region (2.5 μm to 5 μm) and light in a wavelength region (2.5 μm or less) shorter than a near-infrared wavelength region. Further, a λ/4 plate 20 is arranged on an optical path between the dichroic mirror 31 and an optical scanner 26. Light transmitted through the dichroic mirror 31 is formed as an image by a lens 22 and imaged by the infrared camera 30. On the other hand, light reflected by the dichroic mirror 31 is detected by a photodetector 13 via the λ/4 plate 20, the optical scanner 26, and a PBS 19. The dichroic mirror 31 also serves to shield infrared rays so that light in the infrared wavelength region is not output to an optical path directed toward the photodetector 13. In the analysis system 1A, a heat source position is identified while switching between an infrared imaging mode in which infrared rays from a heat source are detected by the infrared camera 30 and an optical probing mode in which reflected light is detected by the photodetector 13, or at the same time as the switching (which will be described below in detail).

In the infrared imaging mode, the infrared camera 30 sets energy of black body radiation of which a color of radiated light changes according to a temperature as a measurement object. In this embodiment, the infrared camera 30 identifies a position in a plane direction (X-axis and Y-axis directions in FIGS. 5 and 6) perpendicular to an optical axis direction (a Z-axis direction in FIGS. 5 and 6) of the irradiated light among heat source positions. If the infrared camera 30 detects (images) heat generated by the heat source inside the measurement object MO as infrared rays, the infrared camera 30 outputs a detection signal (an infrared image) to a computer 15.

The computer 15 reads the detection signal (the infrared image) to identify an X coordinate and a Y coordinate of a point at which the amount of heat is largest on the surface of the measurement object MO (that is, a point directly over the heat source), as an X-coordinate and a Y-coordinate of the heat source. After the X coordinate and the Y coordinate of the heat source are identified in this manner, a condition setting unit 15*c* sets a measurement point on the surface of the measurement object MO. In this case, the identified X and Y coordinates of the heat source may be set as the measurement point, and a plurality of measurement points may be set at the X coordinate and the Y coordinate of the heat source or around the coordinates.

Then, in the optical probing mode, the measurement point set by the condition setting unit 15*c* is irradiated with light, and reflected light is measured by the photodetector 13. In this case, a phase delay amount of a detection signal input from the photodetector 13 to a processing unit 14 and further input from the processing unit 14 to a data analysis unit 15*a* is derived at the set measurement point. Hereinafter, identification of the heat source position by the data analysis unit 15*a* will be described with reference to FIG. 6.

Figure 6:
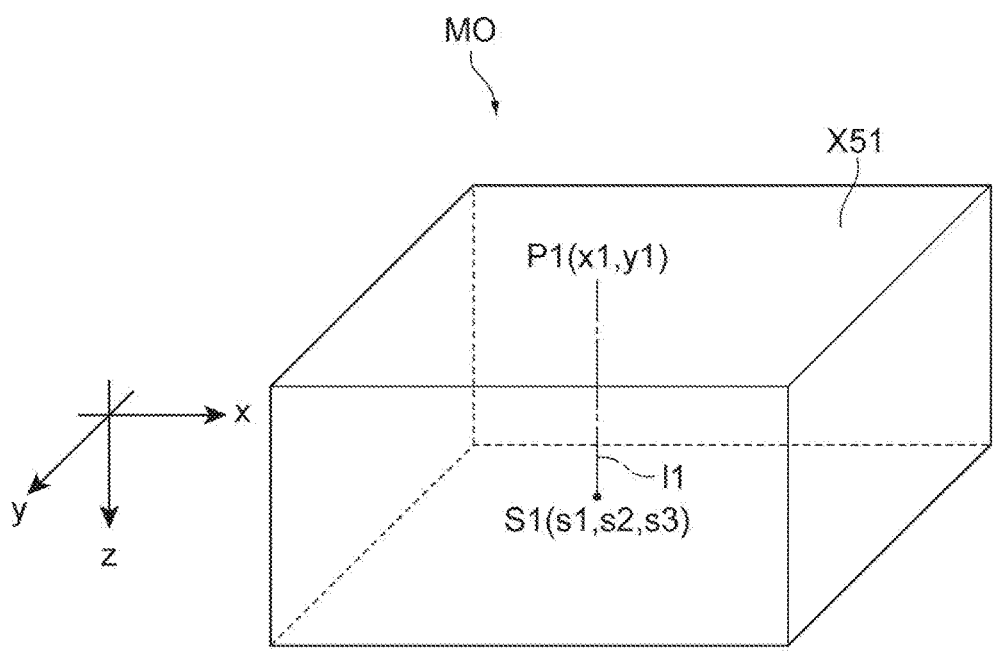
FIG. 6 is a diagram illustrating an analysis image of a heat source position by one-point measurement.

FIG. 6 is a diagram schematically illustrating only a portion of the measurement object MO in the semiconductor device SD. The computer 15 reads the detection signal (the infrared image) input from the infrared camera 30 in a state in which the analysis system 1A enters the infrared imaging mode to acquire an X-coordinate and Y-coordinate (s1, s2) of the heat source S1, and sets the X coordinate and Y coordinate (s1, s2) of a heat source S1 for the measurement point.

Subsequently, the analysis system 1A is switched to the optical probing mode, a set measurement point P1 (s1, s2) is irradiated with light, and the detection signal from the photodetector 13 is input to the data analysis unit 15*a* via the processing unit 14. In the data analysis unit 15*a*, the respective parameters (v (m/s): heat propagation velocity, f (kHz): frequency of a modulation current, K (W/m/k): thermal conductivity of the measurement object MO, q (J/g/k): specific heat of the measurement object MO, and ρ (kg/m$^-$$_3$): density of the measurement object MO) of Equation (1) described above are set, and the heat propagation velocity is calculated and stored. The data analysis unit 15*a* derives a phase delay amount of the detection signal based on a detection signal converted from reflected light from the measurement point P1 and the modulation current (a timing trigger signal). Further, the data analysis unit 15*a* derives a distance 11 from the measurement point P1 to a heat source S1 based on the phase delay amount and the stored heat propagation velocity.

Here, since the measurement point P1 is the X coordinate and Y coordinate (s1, s2) of the heat source S1, the data analysis unit 15*a* can derive a position in the Z-axis direction (an optical axis direction; a depth direction) of the heat source S1 based on the distance 11 from the measurement point P1 to the heat source S1. Thus, coordinates (s1, s2, s3) that are a position of the heat source S1 are identified. Through this process, the data analysis unit 15*a* identifies the heat source position.

The condition setting unit 15*c* may set one point on the surface of the measurement object MO as well as a plurality of measurement points based on the infrared image. In this case, it is preferable to set the measurement points at the heat source S1 or around the heat source S1.

Next, an operation and an effect of the analysis system 1A according to this embodiment will be described.

The analysis system 1A includes the infrared camera 30 that acquires the infrared image of the measurement object MO. Since a rough heat source position can be identified by the infrared camera 30, it is possible to simplify analysis of the heat source position in the data analysis unit 15*a*.

Specifically, the condition setting unit 15*c* sets at least one measurement point by referring to a heat source position in an infrared image based on the infrared image acquired by the infrared camera 30. In this case, the heat source position in the infrared image may be set as the measurement point, or the measurement point may be set around the heat source position. Further, the infrared image may be displayed on a display unit 28, and a user may set the measurement point using an input unit 29. Accordingly, it is possible to perform identification of the heat source position more easily using optical probing.

Further, the data analysis unit 15*a* may determine three or more points on the surface of the measurement object MO surrounding a position in a plane direction identified by the infrared camera 30, as measurement points, and derive a phase delay amount of the detection signal at the three or more measurement points on the surface. Thus, by narrowing down positions in the plane direction of the heat source using the infrared camera 30 and deriving the phase delay amount of the points surrounding the position, it is possible to improve analysis accuracy of the heat source position, for example, in comparison with a case in which the heat source position is analyzed using a phase delay amount derived at three or more random measurement points without using the infrared camera 30. That is, it is possible to analyze the heat source position with higher accuracy.

Further, by using the infrared camera 30, it is possible to easily recognize the number and two-dimensional positions of heat sources (positions in the plane direction) using the infrared camera 30 in advance, for example, in a case in which there are a plurality of heat sources. Further, the three-dimensional position of the heat source may be primarily identified by the infrared camera 30. In this case, accuracy is lower than that of analysis of a heat source position using optical probing. However, it is possible to recognize all images of the plurality of heat sources.

Figure 7:
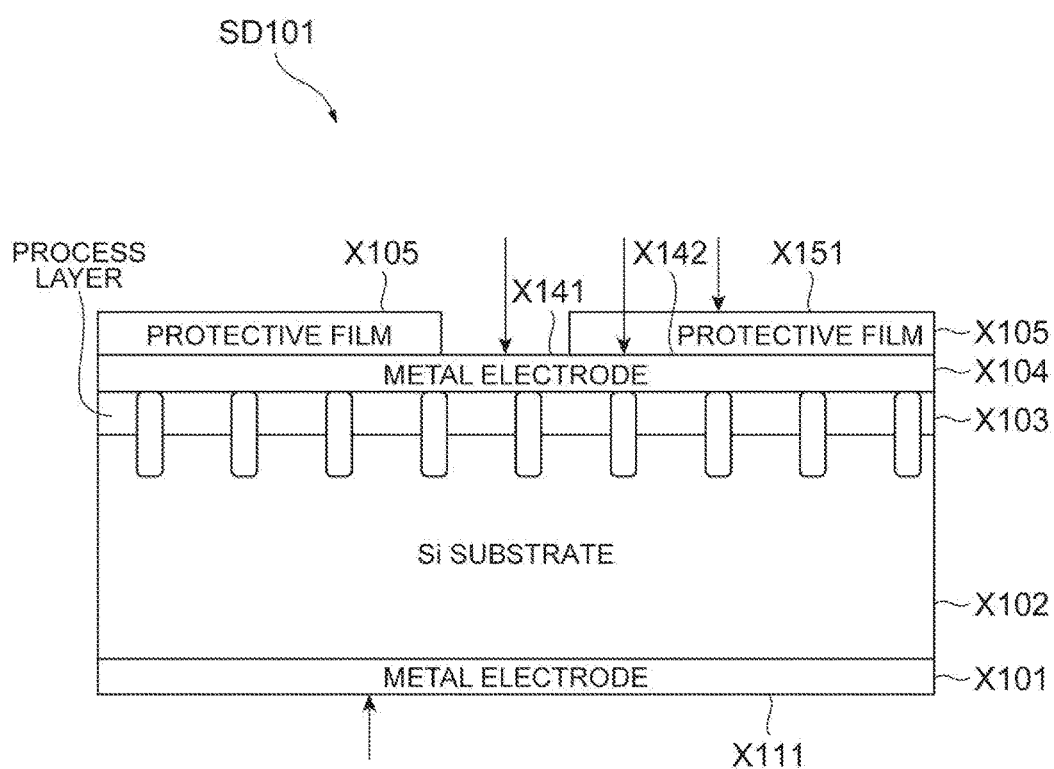
FIG. 7 is a diagram illustrating a semiconductor device according to a modified example.

Although the preferred embodiments of the present invention have been described above, the present invention is not limited to the above embodiments. For example, the measurement object MO may be moved using the stage 25 so that the measurement point set by the condition setting unit 15*c* is irradiated with light. For example, the condition setting unit 15*c* may randomly set a plurality of measurement points for the measurement object MO or may set a plurality of measurement points so that measurement can be performed while scanning an entire or partial region of the measurement object MO. For example, the modulation current output from the tester 11 to the semiconductor device SD and the frequency thereof may be the same, a trigger signal with a synchronized phase may be output from the tester 11 to the processing unit 14, and synchronization with the processing unit 14 may be performed. Further, the semiconductor device SD is not necessarily driven by the modulation current (the stimulation signal) applied by the tester 11, and the modulation current (the stimulation signal) may be applied separately from a driving signal. For example, the example of the semiconductor device SD1 or SD2 that is an integrated circuit has been described as an example of the semiconductor device SD, but the semiconductor device is not limited thereto. For example, the semiconductor device may be a power device SD101 illustrated in FIG. 7. As illustrated in FIG. 7, in the power device SD101, a Si substrate X102 and a process layer X103 are stacked to be sandwiched between metal electrodes X101 and X104. Further, a protective film X105 is stacked on the metal electrode X104. The protective film X105 is not intended to cover an entire surface of the metal electrode X104, and the metal electrode X104 not covered with the protective film X105 is in contact with air. In such a configuration, for example, the metal electrodes X101 and X104 and the Si substrate X102 and the process layers X103 sandwiched between the metal electrodes X101 and X104 are measurement objects. In this case, a surface of the measurement object includes surfaces X111 and X141 of the metal electrodes X101 and X104 which are in contact with air, and a surface X142 of the metal electrode X104 that is in contact with the protective film X105. Further, if the protective film X105 is also included in the measurement object, the surface of the measurement object includes a surface X151 of the protective film X105 that is in contact with air.

REFERENCE SIGNS LIST 1, 1A: Analysis system
11: Tester
12: Light source
13: Photodetector
15a: Data analysis unit
15c: Condition setting unit
26: Optical scanner
30: Infrared camera
MO: Measurement object

The invention claimed is:

1. An analysis system identifying a heat source position inside a measurement object, the analysis system comprising:
   a setting unit configured to set a measurement point for one surface of the measurement object;
   an applying unit configured to apply a stimulation signal to the measurement object;
   a light irradiator configured to irradiate the measurement point with light;
   a light detector configured to detect light reflected from the measurement point and output a detection signal; and
   an analyzer configured to identify the heat source position by deriving a distance from the measurement point to the heat source position based on the detection signal and the stimulation signal.

2. The analysis system according to claim 1,
   wherein the setting unit is configured to set at least three measurement points for the measurement object, and
   the analyzer is configured to derive a distance from each of the at least three measurement points to the heat source position to identify the heat source position.

3. The analysis system according to claim 1,
   wherein the light irradiator comprises a light source configured to output the light and an optical scanner configured to irradiate the measurement point with the light.

4. The analysis system according to claim 1, further comprising:
   an infrared camera configured to acquire an infrared image of the measurement object.

5. The analysis system according to claim 4,
   wherein the setting unit is configured to set the measurement point based on the infrared image.

6. The analysis system according to claim 1,
   wherein the analyzer is configured to derive a phase delay amount of the detection signal relative to the stimulation signal to derive the distance from the measurement point to the heat source position.

7. The analysis system according to claim 6,
   wherein the analyzer is configured to derive the distance from the measurement point to the heat source position based on the derived phase delay amount and a heat propagation velocity that is determined according to the measurement object to analyze the heat source position.

8. The analysis system according to claim 6,
   wherein the analyzer
   is configured to store a table defining a correspondence relationship between the phase delay amount of the detection signal and the distance from the measurement point to the heat source position, and
   derive the distance from the measurement point to the heat source position based on the derived phase delay amount and the table to analyze the heat source position.

9. An analysis method for identifying a heat source position inside a measurement object, the analysis method comprising:
   setting a measurement point for one surface of the measurement object;
   applying a stimulation signal to the measurement object;
   irradiating the measurement point with light;
   converting light reflected from the measurement point into a detection signal; and
   identifying the heat source position by deriving a distance from the measurement point to the heat source position based on the detection signal and the stimulation signal.

10. The analysis method according to claim 9,
    wherein setting a measurement point comprises setting at least three measurement points for the measurement object, and
    identifying the heat source position comprises deriving a distance from each of the at least three measurement points to the heat source position to identify the heat source position.

11. The analysis method according to claim 9, further comprising:
    acquiring an infrared image of the measurement object,
    wherein setting a measurement point comprises setting the measurement point based on the infrared image.

12. The analysis method according to claim 9,
    wherein identifying the heat source position comprises deriving a phase delay amount of the detection signal relative to the stimulation signal to derive the distance from the measurement point to the heat source position.

* * * * *